United States Patent [19]

Yorozu et al.

[11] Patent Number: 5,026,551
[45] Date of Patent: Jun. 25, 1991

[54] BATH ADDITIVE COMPOSITION

[75] Inventors: Hidenori Yorozu; Yasuteru Eguchi; Wataru Ohkawa, all of Utsunomiya; Yasunobu Matsumoto, Ichikai, all of Japan

[73] Assignee: Kao Corporation, Tokyo, Japan

[21] Appl. No.: 1,461

[22] Filed: Jan. 8, 1987

[30] Foreign Application Priority Data

| Jan. 8, 1986 | [JP] | Japan | 61-1779 |
| Jan. 8, 1986 | [JP] | Japan | 61-1780 |
| Oct. 9, 1986 | [JP] | Japan | 61-240248 |

[51] Int. Cl.$^5$ .......................... A61K 7/48; A61K 7/50
[52] U.S. Cl. ...................................... 424/44; 424/46; 424/700
[58] Field of Search ................ 424/44, 161, 131, 43

[56] References Cited

U.S. PATENT DOCUMENTS

| 2,854,377 | 9/1958 | Elias | 424/44 |
| 2,985,562 | 5/1961 | Millard et al. | 424/44 |
| 3,328,307 | 6/1967 | Schmitz | 424/44 |
| 4,650,667 | 3/1987 | Eguchi et al. | 424/44 |
| 4,666,707 | 5/1987 | Eguchi et al. | 424/44 |

FOREIGN PATENT DOCUMENTS

| 55-136215 | 10/1980 | Japan | 424/44 |
| 727196 | 4/1980 | U.S.S.R. | 424/44 |
| 527041 | 10/1940 | United Kingdom | 424/44 |

Primary Examiner—Dale R. Ore
Attorney, Agent, or Firm—Oblon, Spivak, McClelland, Maier & Neustadt

[57] ABSTRACT

A novel weakly acidic bath additive composition comprises carbon dioxide gas or a substance capable of producing carbon dioxide gas and an oily ingredient.

The composition promotes the blood circulation due to the effect of carbon dioxide gas present in the bath water. Further, because of an oily ingredient, the skin is supplied by an oil and provided moistened feel after bathing.

9 Claims, No Drawings

BATH ADDITIVE COMPOSITION

BACKGROUND OF THE INVENTION (1) Field of the Invention

This invention relates to a bath additive composition and, more particularly, to a bath additive composition capable of preventing chilling and providing favorable feeling of skins after taking a bath.

(2) Description of the Prior Art

A bath additive composition generally comprises a mixture of inorganic salts such as salt cake, borax, sulfur and carbonate incorporated with perfumes, colorants, extracts of herbs and organic acids, which provides bath water with fragrances or colors and stimulates skin surfaces moderately, thereby activating the blood circulation to promote the recovery from fatigue and metabolism. Among bath additive compositions, there have been known bubbling bath additive compositions comprising a carbonate and an acid in combination, which evolve bubbles of carbon dioxide gas. The bubbles enhance relaxing and refreshing feelings, and render a bath enjoyable.

However, since the conventional bubbling bath additive compositions are neutral or weakly alkaline and most of carbon dioxide gas evolved do not dissolve in water but evaporate into air, the gas bubbles of carbon dioxide simply provide a sense of mechanical actions.

The present inventors have previously reported a weakly acidic bath additive composition containing a carbonate and an acid, which makes bath water to be weakly acidic, thereby holding gaseous carbon dioxide in the bath water, promoting blood circulation and not causing chilling after taking bath.

However, there has been demanded such a bath additive composition that further provides favorable feelings of skins after taking a bath in addition to the above described bathing effect.

SUMMARY OF THE INVENTION

The present inventors made an earnest study for solving the foregoing problems and, as a result, accomplished this invention based on the finding that an excellent bath additive composition can be obtained by adding an oily ingredient together with carbon dioxide gas or a substance capable of producing carbon dioxide gas, thereby providing a weakly acidic nature.

That is, this invention provides a weakly acidic bath additive composition comprising carbon dioxide gas or a substance producing carbon dioxide gas and an oily ingredient.

In this invention, carbon dioxide gas carried by a carbon dioxide gas-holding substance such as alumino silicate and cyclodextrin, or sealed under a high pressure is used.

DETAILED DESCRIPTION OF THE INVENTION AND PREFERRED EMBODIMENTS

Any of amorphous, partially crystallized or crystallized type alumino silicates may be used as a carbon dioxide gas-holding substance. Of these, crystallized type is preferred. Examples of such alumino silicates include natural alumina silicates such as analcite and rhombic zeolite and synthetic zeolites referred to as zeolites A, X and Y. Among all, the synthetic zeolites with less impurities represented by the following general formula are preferred:

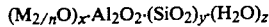

in which M represents a metal atom having a valence of n, x is a number of from 0.7 to 1.5, y is a number of from 0.8 to 10 and z is a number greater than 0.

Among the synthetic zeolites of the above general formula, the metal atom represented by M includes sodium, potassium, calcium, magnesium and the like. It is preferred that z is 0, that is, no substantial water is contained. The particle size of the alumino silicate is from 0.5 to 100 $\mu$m and, preferably, from 1 to 40 $\mu$m. The substance for holding the carbon dioxide gas is used in the form of fine powder having the particle size as described above, granule or pellet. Of these, fine powder is preferred in view of the effect to be obtained.

Cyclodextrin as a carbon dioxide gas-holding substance includes $\alpha$-cyclodextrin, $\beta$-cyclodextrin, $\gamma$-cyclodextrin and derivatives thereof.

Carbon dioxide gas is adsorbed to these gas-holding substances, for example, by bringing the gas-holding substance into contact with carbon dioxide gas. The gas-holding substance such as alumino silicate is used, preferably, in the form of dehydrated by heat treatment and, most preferably, in the form of containing no substantial water. The adsorption is carried out preferably under anhydrous condition and at a gas pressure of carbon dioxide of greater than 0.1 kg/cm$^2$, preferably, from 1 to 10 kg/cm$^2$. The temperature is lower than 30° C., preferably, lower than 20° C. There is no particular restriction for the time and the adsorption is preferably carried out till the system reaches an equillibrium.

The amount of the carbon dioxide gas adsorbed to the gas-holding substance is more than 2 g CO$_2$/100 g gas-holding substance and, preferably, 5 g CO$_2$/100 g gas-holding substance.

Any of carbon dioxide gas-producing substances that evolve carbon dioxide gas under reaction may be used and, among all, combination of a carbonate and an acid is preferred.

Examples of the carbonate include sodium hydrogen carbonate, sodium sesqui-carbonate, sodium carbonate, potassium hydrogen carbonate, ammonium hydrogen carbonate, magnesium carbonate, calcium carbonate and the like. These carbonates may be used alone or in combination of two or more of them.

Organic or inorganic acids may be used as the acid and those water soluble and solid acids are preferred. The examples of organic acids include dicarboxylic acids such as succinic acid, glutaric acid, adipic acid, pymellic acid and fumaric acid; acidic amino acids such as glutamic acid and aspargic acid; hydro oxyacids such as maleic acid, citric acid and ascorbic acid; benzoic acid, pyrrolidone carboxylic acid and acidic salts of these organic acids. The examples of inorganic acids include potassium dihydrogen phosphate, sodium sulfite and the like. Among all, one or more of acids selected from the acids represented by the formula: HOO-C—(CH$_2$)$_n$—COOH (in which n represents an integer from 2 to 4) and fumaric acid are preferred.

It is required for the weakly acidic bath additive composition in this invention that the blending amount of the carbonate and the acid is made to such a ratio that the bath water becomes weakly acidic when the bath additive composition is added to the bath water, that is, the pH value of an aqueous solution containing 0.01% by weight of bath additive composition is from 4 to 7 and, preferably, from 6.0 to 6.7. If pH is lower than 4, the bath water stimulates the skins and damages a bath tub and the like. On the other hand, if it exceeds 7, the effects of this invention can not be obtained, because the effect of carbon dioxide gas in this invention is based on the theory that carbon dioxide gas is present as a $CO_2$ molecule and promotes the blood flow in the case where the system is acidic, whereas the carbon dioxide gas is present as $CO_2{}^{2-}$ ion or $HCO_3{}^-$ ion in an alkaline system, so that no such effect is revealed.

The incorporation amounts of the carbonate and the acid for providing such condition depend on the type of them, however from 5 to 80% by weight and, particularly, from 10 to 50% by weight of the carbonate, and from 10 to 80% and, particularly, from 15 to 50% of the acid are preferred.

The oily ingredient used for the bath additive composition according to this invention is insoluble or less soluble to water, liquid or solid at ambient temperature. It is viscous when it is in a liquid state, and has inflammability. Examples of such oily ingredient are as follows:

Oils and Fats:

Natural oils and fats such as soy bean oil, rice barn oil, jojoba oil, avocado oil, almond oil, olive oil, cacao butter, sesame oil, parsic oil, castor oil, coconut oil, mink oil, beef tallow and lard: hardened oils obtained by hydrogenating these natural oils and fats and synthesized triglycerides such as glyceride myristate and 2-ethylhexanoic glyceride.

Waxes:

Carnauba wax, spermaceti, beewax, lanoline and the like.

Hydrocarbons:

Liquid paraffin, vaseline, paraffin, microcrystalline wax, ceresin, squalane, pristane and the like.

Higher fatty acids:

Lauric acid, myristic acid, palmitic acid, stearic acid, behenic acid, oleic acid, linolic acid, linolenic acid, lanolinic acid, isostearic acid and the like.

Higher alcohols:

Lauryl alcohol, cetyl alcohol, stearly alcohol, oleyl alcohol, lanoline alcohol, cholesterol, 2-hexyldecanol and the like.

Esters:

Mirystyl lactate, cetyl lactate, isopropyl myristate, mirystyl miristate, isopropyl palmitate, isopropyl adipate, butyl stearate, decyl oleate and the like.

Silicone oils

These oily ingredients are used alone or in combination of two or more of them and, preferably, incorporated such that the oily ingredient of from 10 to 500 ppm and, particularly, of from 20 to 100 ppm is present when the bath additive composition is placed in a bath water.

In the bath additive composition according to this invention, it is preferred to further incorporate a dispersant or emulsifier for the oily ingredient in addition to the above essential ingredients so that the oily ingredient can be dispersed or emulsified uniformly when the bath additive composition is placed in the bath water. Thus, the oily ingredient can be prevented from floating on the water surface when the bath additive composition is placed in the bath water, as well as the bath water can be turbid to reduce the transparency of an aqueous 0.01% by weight of solution to less than 40 cm and, preferably, to less than 20 cm, thereby creating a high quality image like that of a milk bath. The transparency referred to in this invention is indicated by a depth at which a white disc of 3 cm diameter sinked into water can no more be observed.

The dispersant or emulsifier used for the above purpose may comprise water soluble polymer, surface active agent and the like. The water-soluble polymer includes sodium alginate, propylene glycol alginate ester, gum arabic, gum xanthene, pectine, tragacanth gum, sodium carboxymethyl cellulose, methyl cellulose, carboxyvinyl polymer, polyethylene glycol, polyvinyl alcohol, polyvinyl pyrrolidone, milk protein, soy bean protein, gelatine, egg protein, sodium casein, whey protein and the like. Of these, gums such as gum arabic and gum xanthene and water soluble proteins such as sodium casein and whey protein are preferred. As a surface active agent, anionic, cationic, non-ionic and both of natural and synthetic surface active agents may be used.

The dispersant or the emulsifier for the oily ingresients may preferably be incorporated by 5 to 100% by weight to the oily ingredient in the bath additive composition.

In the bath additive composition according to this invention, it is preferred to further incorporate fine powder of less than 3 $\mu$m of particle size, which has a precipitation ratio of less than 50% by weight in water after 24 hours and is substantially insoluble in water. By well dispersing the fine powder in the bath water, sticky feeling due to the oily ingredient can be suppressed and fresh feeling can be increased after taking a bath.

The fine powder capable of satisfying such conditions may preferably be selected from those generally referred to as a cosmetic powder and they include those fine powders of acrylic resin, styrenic resin, epoxy resin, nylon, polyethylene, polypropylene, polyvinyl chloride, polyethylene terephthalate resin, polytetrafluoroethane, copolymers of these polymers, silicic acid, calcium silicate, natural aluminum silicate, synthetic aluminum silicate, zeolite, titanium oxide, talc, kaolinite, mica and bentonite.

Those fine powders having intrinsic specific gravity of about 1 are preferred and those having higher or lower intrinsic specific gravity are preferably combined, or subjected to melting treatment or surface treatment so as to make their specific gravity to almost 1. The fine powder is preferably incorporated by from 10 to 500% by weight relative to the oily ingredient in the bath additive composition. The precipitation ratio in this invention is obtained by dispersing 0.5 g of the bath additive composition in a No. 6 Ukena colorimeter tube in which water is filled to a height of 30 cm and standing still for 24 hours. Then, completely precipitated powder was dried and weighed.

Further, the bath additive composition according to this invention can be incorporated with herb medicines, colorants, vitamines, perfumes, enzymes and other ingredients required for preparing the bath additive compositions.

The bath additive composition according to this invention is prepared by adding the optional ingredients to the essential ingredients described above as required and adjusting such that the bath water becomes weakly acidic when the composition is placed in a bath water. It may be prepared into granule, tablet and milky lotion, etc.

The bath additive composition according to this invention promotes the blood circulation due to the effect of carbon dioxide gas present in the bath water and exhibits excellent bathing effects. Futher, the oily ingredients in the bath additive composition disperses in a bath water, so that the oil deposits on the skin. Thus, the skin is supplied by an oil and provided moistened feel after bathing.

This invention will now be explained referring to Examples and Test Examples.

EXAMPLE 1

10 parts by weight of DIA (diisopropyl adipate), 10 parts by weight of liquid paraffin, 5 parts by weight of a nonionic surface active agent (trade name: Emulgen 320, manufactured by Kao Corporation), 10 parts by weight calcium silicate and 15 parts by weight of dextrin were well mixed and pulverized by a conventional manner. To 10 parts by weight of the thus obtained powder, 30 parts by weight of sodium hydrogen carbonate, 15 parts by weight of sodium carbonate, 35 parts by weight of succinic acid, 2 parts by weight of polyethylene glycol 6000, 5 parts by weight of sodium sulfate and small amounts of colorant and perfume were added and uniformly mixed. The resultant powder mixture was prepared into tablets of 50 g weight per tablet. The tablets were packed in an aluminum case to prepare a bath additive composition.

COMPARATIVE EXAMPLE 1

30 parts by weight of sodium hydrogen carbonate, 15 parts by weight of sodium carbonate, 35 parts by weight of succinic acid, 2 parts by weight of polyethylene glycol 6000, 5 parts by weight of sodium sulfate, 10 parts by weight of dextrin and small amounts of colorant and perfume were uniformly mixed. The thus obtained powder mixture was prepared into tablets of 50 g weight per tablet. The tablets were packed in an aluminum case to prepare a bath additive composition.

EXAMPLE 2

200 parts by weight of water was added to 5 parts by weight of DIA (diisopropyl adipate), 15 parts by weight of liquid paraffin, 2 parts by weight of whey protein and 40 parts by weight of dextrin, and emulsified by an ordinary method. The thus obtained emulsion was spray-dried to obtain powder. To this powder, 10 parts by weight of acrylic resin[1]), 10 parts by weight of sodium hydrogen carbonate, 5 parts by weight of sodium carbonate, 15 parts by weight of succinic acid, 0.5 parts by weight of polyethylene glycol 6000 and small amounts of colorant and perfume were added and uniformly mixed. The thus obtained powder mixture was prepared into tablets of 50 g weight per tablet. The tablets were packed in an aluminum case to prepare a bath additive composition.

[1] Acrylic resin: precipitated amount after 24 hours: 12%; average particle size: 0.4; maximum particle size: less than 1.

COMPARATIVE EXAMPLE 2

200 parts by weight of water was added to 5 parts by weight of DIA, 15 parts by weight of liquid paraffin, 2 parts by weight of whey protein and 40 parts by weight of dextrin and emulsified by an ordinary method. The thus obtained emulsion was spray-dried to obtain powder.

To this powder, 20 parts by weight of sodium sulfate, 20 parts by weight of sodium hydrogen carbonate and small amounts of colorant and perfume were added and uniformly mixed. The obtained powder was weighed 50 g for one pack and prepared into a powdery bath additive composition.

TEST EXAMPLE

The bath additive compositions obtained in Examples 1 and 2 and Comparative Examples 1 and 2 were used by a common method by 20 panelists for 10 days to examine the overall estimation (collective feelings upon use), moistened feeling to the skins, refreshed feeling after taking a bath and the condition of the bath water. The results are shown in Table 1.

It can be seen that the bath additive compositions according to this invention are excellent in that they moisten the skins and provide refresh feeling after taking a bath, as well as provide favorable state of bath water.

TABLE 1

| Comparison | Evaluation | Inventive composition is better | No particular selection | Comparative composition is better |
|---|---|---|---|---|
| Comparison between Example 1 and Comparative Example 1 | Overall evaluation | 14 | 5 | 1 |
| | Moistened feeling to skin | 13 | 7 | 0 |
| | Refresh feeling to skin | 11 | 7 | 2 |
| | Preference bath water state | 14 | 5 | 1 |
| Comparison between Example 2 and Comparative Example 2 | Overall evaluation | 13 | 4 | 3 |
| | Moistened feeling to skin | 16 | 4 | 0 |
| | Refresh feeling to skin | 14 | 5 | 1 |
| | Preference bath water state | 10 | 6 | 4 |

EXAMPLE 3

200 parts by weight of water was added to 3 parts by weight of cetanol, 17 parts by weight of liquid paraffin, 5 parts by weight of glyceride monostearate, 2 parts by weight of sodium casein and 40 parts by weight of dextrin and emulsified by an ordinary method. The thus obtained emulsion was spray dried to obtain a powder. To this powder, 10 parts by weight of acrylic resin (same as in Example 2), 10 parts by weight of sodium hydrogen carbonate, 5 parts by weight of sodium carbonate, 15 parts by weight of succinic acid, 1 part by weight of polyethylene glycol 6000 and small amounts of colorant and perfume were added and uniformly mixed. Then, thus obtained powder mixture was prepared into tablets of 80 g weight per tablet. The tablets were packed in an aluminum case to prepare a bath additive composition.

EXAMPLE 4

After uniformly mixing the powder obtained by the formulation of Example 3, it was granulated by a dry ganulating machine to prepare into a granular bath additive composition 80 g each in pack.

What is claimed is:

1. A weakly acidic bath additive composition comprising:
   (1) carbon dioxide gas or a mixture of a carbonate and an acid capable of producing carbon dioxide gas,
   (2) an oily ingredient which is liquid or solid at ambient temperature in an amount effective to provide a moistened feel on the skin,
   (3) an effective amount of a dispersant or emulsifier, and
   (4) fine powder having particle size of less than 3μm, a precipitation ratio in water after 24 hours of less than 50 wt % and substantially insoluble in water, in an amount effective when dispersed in a bath water to suppress the sticky feeling due to the oily ingredient and to increase the fresh feeling after taking a bath.

2. A weakly acidic bath additive composition as defined in claim 1, wherein said oily ingredient is capable of providing moistened feel after bathing.

3. A weakly acidic bath additive composition as defined in claim 1, wherein said oily ingredient is selected from the group consisting of oils, fats, hydrocarbons, higher alcohols, and esters.

4. A weakly acidic bath additive composition as defined in 1, 2, or 3, wherein said substance capable of producing carbon dioxide comprises 5 to 80% by weight of a carbonate and 10 to 80% by weight of at least one acid.

5. A weakly acidic bath additive composition as defined in claim 4, wherein said acid comprises one or more acids selected from the group consisting of an acid represented by the formula:

$$HOOC-(CH_2)_n-COOH$$

in which n represents an integer of from 2 to 4, and fumaric acid.

6. A weakly acidic bath additive composition as defined in claims 1, 2 or 3, wherein said carbon dioxide gas is carried by zeolite or cyclodextrin.

7. A weakly acidic bath additive composition as defined in claim 1, which when dissolved in a bath water results in the pH of said bath water to be 4–6.7, the amount of said oily ingredient in said bath water to be 10–500 ppm and the amount of said carbon dioxide gas in said bath water to be 50–100 ppm.

8. A weakly acidic bath additive composition as defined in claim 1, wherein the amount of said dispersant or emulsifier is 5–100% by weight relative to said oily ingredient.

9. A weakly acidic bath additive composition as defined in claim 1, wherein the amount of said fine powder is 10–500% by weight relative to said oily ingredient.

* * * * *